United States Patent [19]
Rackur et al.

[11] Patent Number: 5,773,447
[45] Date of Patent: Jun. 30, 1998

[54] COMPOUNDS FOR TREATING DISORDERS OF LIPID METABOLISM AND THEIR PREPARATION

[75] Inventors: Gerhard Rackur, Idstein; Hans Georg Böger, Waldems Esch; Norbert Krass, Frankfurt; Axel Hoffmann, Frankfurt; Michael Leineweber, Frankfurt, all of Germany

[73] Assignee: Hoechst Aktiengesellschaft, Frankfurt am Main, Germany

[21] Appl. No.: 874,255

[22] Filed: Jun. 13, 1997

[30] Foreign Application Priority Data

Jun. 24, 1996 [DE] Germany ............... 196 25 088.9

[51] Int. Cl.$^6$ .................. A61K 31/505; C07D 239/02
[52] U.S. Cl. ........................... 514/275; 544/325
[58] Field of Search ............... 514/275; 544/325

[56] References Cited

U.S. PATENT DOCUMENTS

| 4,285,946 | 8/1981 | Kampe et al. | 424/251 |
|---|---|---|---|
| 4,705,792 | 11/1987 | Granzer et al. | 514/275 |
| 5,571,816 | 11/1996 | Kampe et al. | 514/275 |

FOREIGN PATENT DOCUMENTS

| 0 206 297 | 12/1986 | European Pat. Off. . |
|---|---|---|
| 0 557 877 A1 | 9/1993 | European Pat. Off. . |
| 0 557 879 | 9/1993 | European Pat. Off. . |
| 0 557 879 A1 | 9/1993 | European Pat. Off. . |
| 28 53 220 A1 | 7/1980 | Germany . |

OTHER PUBLICATIONS

Hoffmann et al., Biochim. Biophys. Acta (1996), 1299(1), 95–102.

Huettinger et al., Arterioscler. Thromb. (1993), 13(7), 1005–12.

Chomczynski et al., "Single–Step Method of RNA Isolation by Acid Guanidinium Thiocyanate–Phenol–Chloroform Extraction", Analytical Biochemistry, vol. 162, (1987), pp. 156–159.

Meier et al., "Hepatic Monooxygenase activities in Subjects with a Genetic Defect in Drug Oxidation", Gastroenterology, vol. 85, (1983), pp. 682–92.

Lu et al., "Partial Purification of Cytochromes P–450 and P–448 from Rat Liver Microsomes", vol. 46, No. 3, (1972), 1334–1339.

Gervasi et al., "The Metabolism of 1,3–cyclohexadiene by Liver Microsomal Mono–oxygenase", Xenobiotica, vol. 12, No. 8, (1982), pp. 517–526.

Organic Syntheses, vol. V, (1973), pp. 171–173.

Primary Examiner—Mukund J. Shah
Assistant Examiner—Bruck Kifle
Attorney, Agent, or Firm—Foley & Lardner

[57] ABSTRACT

The present invention relates to tertiary 4-amino-2-ureidopyrimidine-5-carboxamides of formula I:

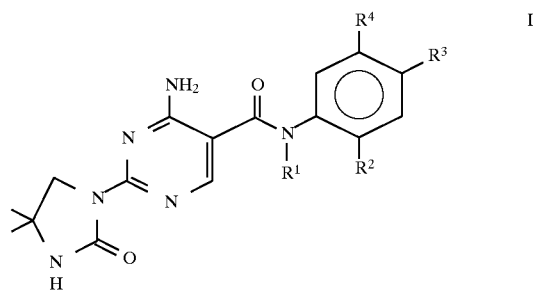

in which $R^1$ is $(C_1-C_8)$-alkyl wherein one or more H are replaced by F; $R^2$ is selected from the group consisting of F, Cl, Br, H, —O—$(C_1-C_8)$-alkyl and $(C_1-C_8)$-alkyl, wherein one or more of the H of the alkyls can be replaced by F; $R^3$ is selected from the group consisting of F, Cl, Br, H, —O—$(C_1-C_4)$-alkyl and $(C_1-C_4)$-alkyl, wherein one or more of the H of the alkyl can be replaced by F; $R^4$ is $CF_3$ or $OCF_3$; and their physiologically tolerable salts. Process for preparing the compounds of formula I are also described. The compounds are suitable for the treatment of disorders of lipid metabolism.

15 Claims, No Drawings

COMPOUNDS FOR TREATING DISORDERS OF LIPID METABOLISM AND THEIR PREPARATION

BACKGROUND OF THE INVENTION

The invention relates to tertiary amides of 4-amino-2-ureidopyrimidine-5-carboxylic acid and their acid addition salts. In particular, the invention relates to substituted 4-amino-2-(imidazolidin-2-on-1-yl)pyrimidine-5-N-(fluoroalkyl)-N-(substituted)phenylcarboxamides and their acid addition salts.

It has already been described to use 4-amino-2-ureidopyrimidine-5-N-(alkyl-N-phenyl)carboxamides for the treatment of adiposity and disorders of lipid metabolism [cf. European Patent 0 557 879]. The metabolic stability of the N-phenylamides proposed as pharmaceuticals, and, in fact, of the alkyl-substituted, tertiary amides, however, is not completely satisfactory. A high stability in the metabolism is very important in order to exclude as far as possible side effects due to metabolites.

SUMMARY OF THE INVENTION

The invention is based on the object of making available compounds which have a high stability in the metabolism and a therapeutically utilizable action in disorders of lipid metabolism, in particular a hypolipidemic action.

Therefore, according to one aspect of the invention, tertiary 4-amino-2-ureidopyrimidine-5-carboxamide compounds of formula I are provided:

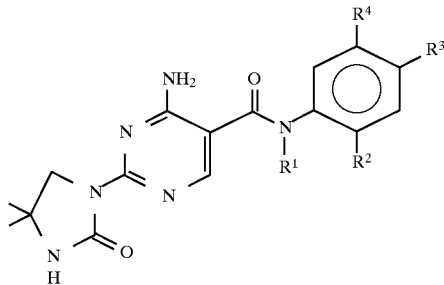

wherein $R^1$ is $(C_1-C_8)$-alkyl wherein one or more or all hydrogens are replaced by fluorine, $R^2$ is selected from the group consisting of fluorine, chlorine, bromine, hydrogen, —O—$(C_1-C_8)$-alkyl and $(C_1-C_8)$-alkyl, wherein one or more or all of the hydrogens of the alkyl radical optionally are replaced by fluorine, $R^3$ is selected from the group consisting of fluorine, chlorine, bromine, hydrogen, —O—$(C_1-C_4)$-alkyl and $(C_1-C_4)$-alkyl, wherein one or more or all of the hydrogens of the alkyl radical optionally are replaced by fluorine, $R^4$ is $CF_3$ or $OCF_3$, or their physiologically tolerable acid addition salts.

According to another aspect of the invention, a process of preparing the inventive compounds according to formula I is provided. This process comprises the following reaction scheme:

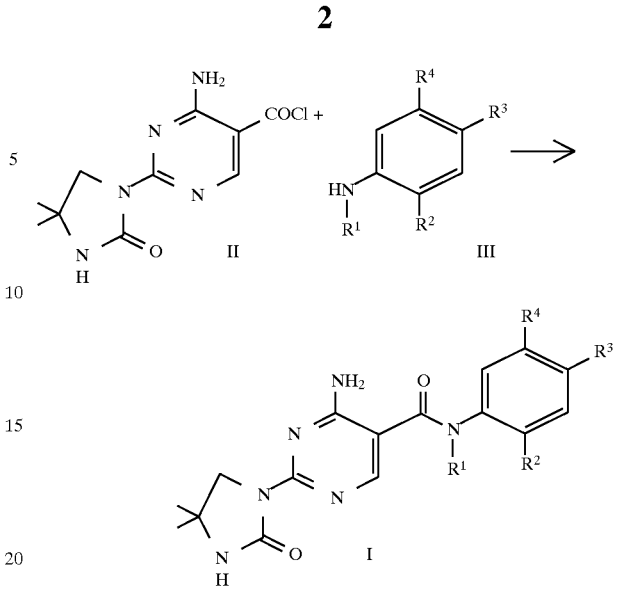

which includes reacting a compound of formula II with a compound of formula III, wherein $R^1$, $R^2$, $R^3$ and $R^4$ are as defined above, at a temperature from 0° C. to 200° C. in a suitable solvent to give a compound of the formula I, and optionally converting the compound of the formula I obtained into a physiologically tolerable salt or converting a salt obtained into a physiologically tolerable salt.

According to yet another aspect of the invention, another process of preparing the compounds of formula I is

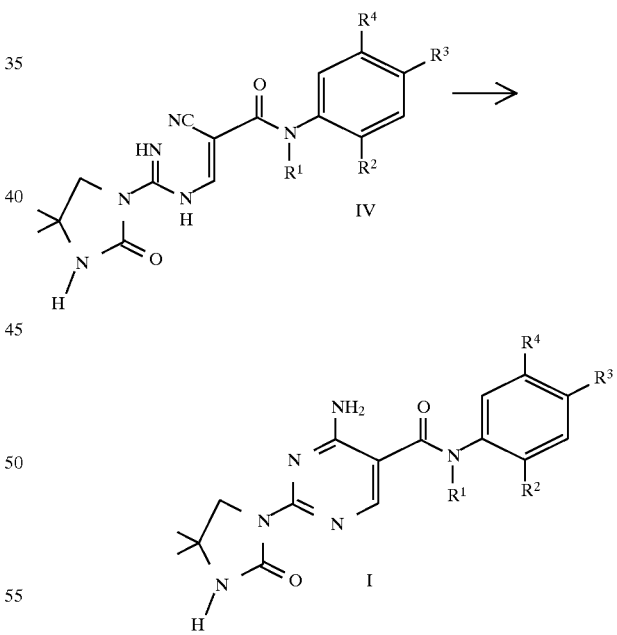

provided. This process comprises the following reaction scheme:

which involves cyclizing a compound of formula IV, wherein $R^1$, $R^2$, $R^3$ and $R^4$ are as defined above, to a form a compound of formula I.

According to yet an additional aspect of the invention, another process for preparing the compounds of formula I is provided. This process comprises the following reaction scheme:

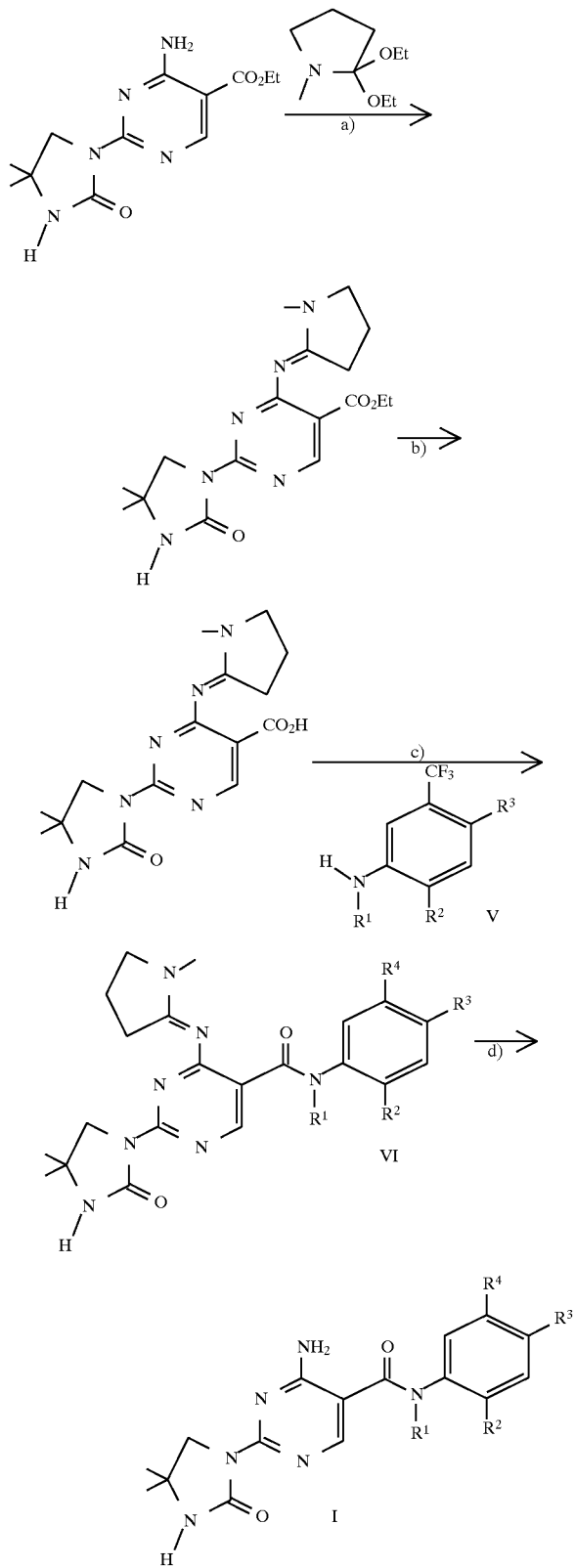

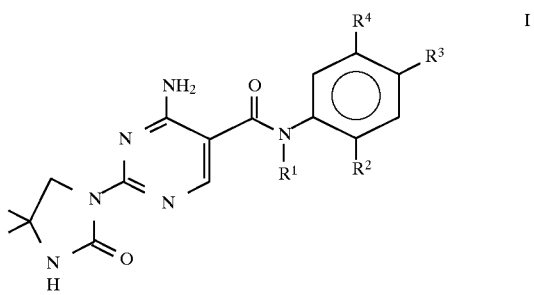

This process involves (a) reacting ethyl 4-amino-2-(4,4-dimethylimidazolidin-2-on-1-yl)-pyrimidinecarboxylate with 2,2-diethoxy-1-methylpyrrolidine in a suitable solvent, at a temperature from 0° to 150° C., to give ethyl 4-(1-methylpyrrolidin-2-ylideneamino)-2-(4,4-dimethylimidazolidin-2-on-1-yl)-pyrimidine-5-carboxylate, (b) reacting the ethyl 4-(1-methylpyrrolidin-2-ylideneamino)-2-(4,4-dimethylimidazolidin-2-on-1-yl) pyrimidine-5-carboxylate obtained with NaI and TMSCl in a suitable solvent at a temperature from 0° to 150° C. to give 4-(1-methylpyrrolidin-2-ylideneamino)-2-(4,4-dimethylimidazolidin-2-on-1-yl)-pyrimidine-5-carboxylic acid, (c) reacting the resulting 4-(1-methylpyrrolidin-2-ylideneamino)-2-(4,4-dimethyl-imidazolidin-2-on-1-yl)-pyrimidine-5-carboxylic acid in a suitable solvent at a temperature from 0° to 150° C., in the presence of TOTU and an auxiliary base, with a compound of formula V to form a compound of formula VI, wherein $R^1$, $R^2$, $R^3$ and $R^4$ are as defined above, and (d) reacting the resulting compound of formula VI, wherein $R^1$, $R^2$, $R^3$ and $R^4$ are as defined above, in a suitable solvent, at a temperature of 0°–150° C. in the presence of an auxiliary base to give a compound of the formula I.

According to a further aspect of the invention, pharmaceutical preparations are provided which comprise compounds of formula I.

According to an additional aspect of the invention, methods of treating disorders of lipid metabolism are provided which comprise administering to a patient an effective amount of at least one compound according to formula I.

Further objects, features and advantages of the present invention will become apparent from the detailed description of preferred embodiments which follows.

DETAILED DESCRIPTION OF THE PREFERRED EMBODIMENTS

Surprisingly, the present inventors have found that tertiary 4-amino-2-ureido-pyrimidine-5-(N-phenyl)carboxamides, whose amide nitrogen atom is disubstituted, i.e. besides the substituted phenyl radical carries a further radical, including a fluoroalkyl radical, display a good lipid-lowering action. The inventive compounds also have an increased stability in the metabolism with respect to metabolic dealkylation.

The invention relates to 4-Amino-2-ureidopyrimidine-5-carboxamides, processes for their preparation, pharmaceuticals comprising these compounds, and methods for their use.

Compounds of the Invention

The inventive 4-amino-2-ureidopyrimidine-5-carboxamide compounds are described by reference to the formula I:

in which $R^1$ is $(C_1-C_8)$-alkyl wherein one or more or all hydrogens are replaced by fluorine, $R^2$ is selected from the group consisting of fluorine, chlorine, bromine, hydrogen, —O—$(C_1-C_8)$-alkyl and $(C_1-C_8)$-alkyl, wherein one or more or all of the hydrogens of the alkyl radical optionally are replaced by fluorine, R³ is selected from the group consisting of fluorine, chlorine, bromine, hydrogen, —O—($C_1$–$C_4$)-alkyl and ($C_1$–$C_4$)-alkyl, wherein one or more or all of the hydrogens of the alkyl radical optionally are replaced by fluorine, R is $CF_3$ or $OCF_3$, and their physiologically tolerable acid addition salts.

Preferred compounds of the formula I are those in which one or more radical(s) has or have the following meaning:

$R^1$ is ($C_1$–$C_4$)-alkyl wherein one or more or all hydrogens are replaced by fluorine, $R^2$ is selected from the group consisting of fluorine, chlorine, hydrogen, —O—($C_1$–$C_4$)-alkyl, and ($C_1$–$C_4$)-alkyl, wherein one or more or all of the hydrogens of the alkyl radical optionally are replaced by fluorine, $R^3$ is selected from the group consisting of fluorine, chlorine, bromine, hydrogen, —O—($C_1$–$C_4$)-alkyl and ($C_1$–$C_4$)-alkyl, wherein one or more or all of the hydrogens of the alkyl radical optionally are replaced by fluorine, $R^4$ is $CF_3$, or $OCF_3$, and their physiologically tolerable acid addition salts.

Particularly preferred compounds of the formula I are those in which one or more radical(s) has or have the following meaning:

$R^1$ is selected from the group consisting of trifluoromethyl, 2,2,2-trifluoroethyl, 2,2,3,3,3-pentafluoropropyl and 2,2,3,3,3,4,4,4-heptafluorobutyl;

$R^2$ is selected from the group consisting of fluorine, chlorine, hydrogen, —$CF_3$ and —$OCF_3$;

$R^3$ is selected from the group consisting of fluorine, chlorine, hydrogen, —$CF_3$ and —$OCF_3$; and $R^4$ is $CF_3$, and their physiologically tolerable acid addition salts.

Specific preferred inventive compounds include 4-Amino-2-(4,4-dimethylimidazolidin-2-on-1-yl)pyrimidine-5-N-(2,2,2-trifluoroethyl)-N-[(3-trifluoromethyl)phenyl]carboxamide hydrochloride, 4-Amino-2-(4,4-dimethylimidazolidin-2-on-1-yl)pyrimidine-5-N-(2,2,3,3,4,4,4-heptafluorobutyl)-N-[(3-trifluoromethyl)phenyl]carboxamide hydrochloride, 4-Amino-2-(4,4-dimethylimidazolidin-2-on-1-yl-pyrimidine-5-N-(2,2,3,3,3-pentafluoropropyl)-N-[(3-trifluoromethyl)phenyl]carboxamide hydrochloride, 4-Amino-2-(4,4-dimethylimidazolidin-2-on-1-yl)pyrimidine-5-N-(2,2,3,3,4,4,4-heptafluorobutyl)-N-[(3-trifluoromethyl)phenyl]carboxamide hydrochloride, 4-Amino-2-(4,4-dimethylimidazolidin-2-on-1-yl)pyrimidine-5-N-(2,2,2-trifluoroethyl)-N-[(3-trifluoromethoxy)phenyl]carboxamide, 4-Amino-2-(4,4-dimethylimidazolidin-2-on-1-yl)pyrimidine-5-N-(2,2 2-trifluoroethyl)-N-[(4-fluoro-3-trifluoromethyl)phenyl] carboxamide, 4-Amino-2-(4,4-dimethylimidazolidin-2-on-1-yl)pyrimidine-5-N-(2,2,3,3,3-pentafluoropropyl)-N-[(3-trifluoromethoxy)phenyl]carboxamide hydrochloride, 4-Amino-2-(4,4-dimethylimidazolidin-2-on-1-yl)pyrimidine-5-N-[(4-chloro-3-trifluoromethyl)phenyl]-N-(2,2,2-trifluoroethyl)carboxamide hydrochloride, 4-Amino-2-(4,4-dimethylimidazolidin-2-on-1-yl)pyrimidine-5-N-[(4-chloro-3-trifluoromethyl)phenyl]-N-(2,2,3,3,3-pentafluoropropyl) carboxamide, 4-Amino-2-(4,4-dimethylimidazolidin-2-on-1-yl)pyrimidine-5-N-[(4-chloro-3-trifluoromethyl) phenyl]-N-(2,2,3,3,4,4,4-heptafluorobutyl)carboxamide, 4-Amino-2-(4,4-dimethylimidazolidin-2-on-1-yl)pyrimidine-5-N-[(6-chloro-3-trifluoromethyl)phenyl]-N-(2,2,3,3,3-pentafluoropropyl)carboxamide hydrochloride, 4-Amino-2-(4,4-dimethylimidazolidin-2-on-1-yl)pyrimidine-5-[N-(3-trifluoromethylphenyl)-N-(2-fluoroethyl)]carboxamide, 4-Amino-2-(4,4-dimethylimidazolidin-2-on-1-yl) pyrimidine-5-[N-(2,2,2-trifluoroethyl)-N-(3-trifluoromethyl-6-chlorophenyl)]carboxamide, 4-Amino-2-(4,4-dimethylimidazolidin-2-on-1-yl)pyrimidine-5-[N-(3-trifluoromethyl-6-chlorophenyl)-N-(2,2,3,3,4,4,4-heptafluorobutyl)]carboxamide, 4-Amino-2-(4,4-dimethylimidazolidin-2-on-1-yl)pyrimidine-5-[N-(3-trifluoromethylphenyl)-N-(2,2,3,3,4,4,5,5,5-nonafluoropentyl)]carboxamide, 4-Amino-2-(4,4-dimethylimidazolidin-2-on-1-yl)pyrimidine-5-[N-(3-trifluoromethylphenyl)-N-(2,2,2-trifluoroethyl)]carboxamide, 4-Amino-2-(4,4-dimethylimidazolidin-2-on-1-yl) -5-pyrimidine-5-[N-(3-trifluoromethyl-4-fluorophenyl)-N-(2,2,3,3,4,4,4-heptafluorobutyl)]-carboxamide, 4-Amino-2-(4,4-dimethylimidazolidin-2-on-1-yl)pyrimidine-5-[N-(2-fluoro-5-trifluoromethylphenyl)-N-(2,2,2-trifluoroethyl)]carboxamide hydrochloride, 4-Amino-2-(4,4-dimethylimidazolidin-2-on-1-yl) pyrimidine-5-[N-(2-fluoro-5-trifluoromethylphenyl)-N-(2, 2,3,3-3-pentafluoropropyl)]carboxamide, 4-Amino-2-(4,4-dimethylimidazolidin-2-on-1-yl)pyrimidine-5-(N-pentafluoropropyl-N-3-trifluoromethyl-4-fluorocarboxanilide), 4-Amino-2-(4,4-dimethylimidazolidin-2-on-1-yl)pyrimidine-5-(N-heptafluoropropyl-N-3-trifluoromethyl-6-fluorocarboxanilide), 4-Amino-2-(4,4-dimethylimidazolidin-2-on-2-yl)pyrimidine-5-N-[(3-trifluoromethylphenyl)-N-(2-fluoroethyl)]carboxamide, and physiologically tolerable salts thereof.

Physiologically tolerable acid addition salts are understood as meaning compounds which are easily soluble, soluble or sparingly soluble in water according to the definition in the "Deutsches Arzneibuch" [German Pharmacopoeia] (9th Edition 1986, Official Issue, Deutscher Apotheker-Verlag Stuttgart), page 19. The hydrochlorides and sulfates of the compounds are preferred.

Processes of the Invention

The invention further relates to three processes for the preparation of 4-amido-2-ureidopyrimidine-5-carboxamides of formula I. These processes are depicted below as processes A, B and C.

Process A

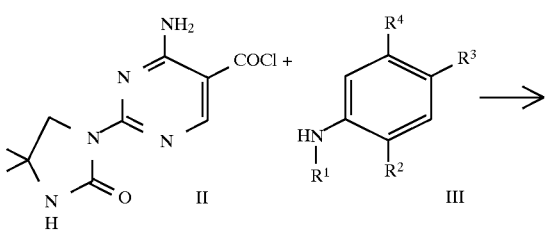

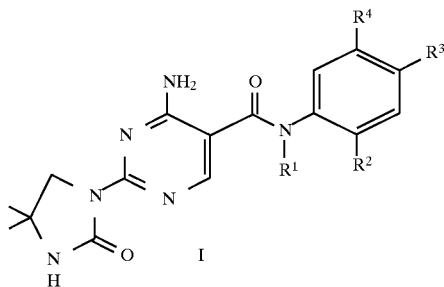

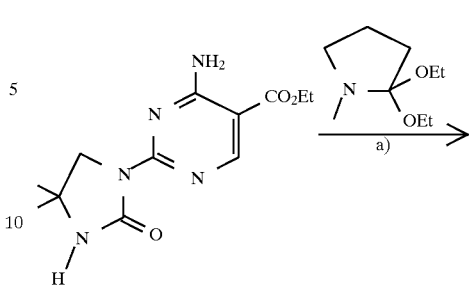

Process A for the preparation of the compounds of formula I comprises reacting a compound of the formula II with a compound of the formula III, in which $R^1$, $R^2$, $R^3$ and $R^4$ have the meanings indicated for formula I, at a temperature from 0° C. to 200° C. in a suitable solvent (such as, for example, DME) with or without addition of an auxiliary base (such as, for example, $NEt_3$) to give a compound of the formula I, optionally converting a compound of the formula I which is obtained into a physiologically tolerable salt or optionally converting a salt which is obtained into a physiologically tolerable salt.

Process B

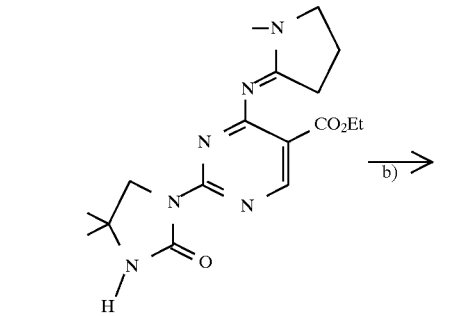

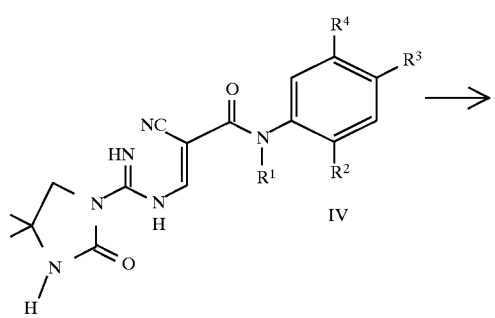

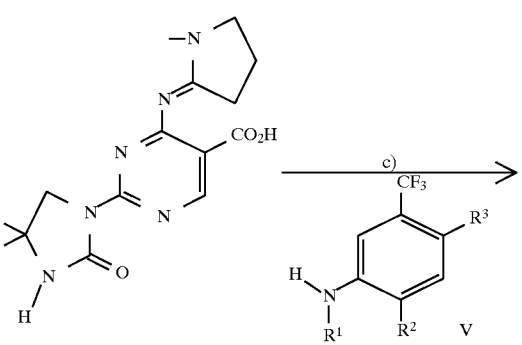

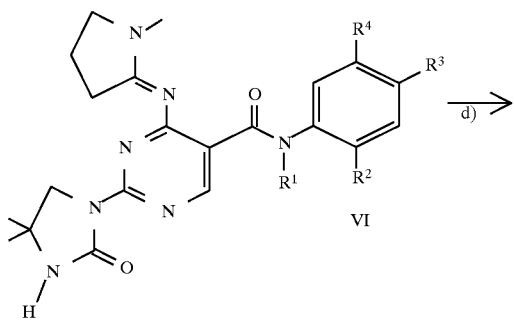

Process B for the preparation of the compounds of the formula I comprises cyclizing a compound of the formula IV, in which $R^1$, $R^2$, $R^3$ and $R^4$ have the meanings indicated for formula I, to a compound of the formula I. The preparation of the compounds of type IV, and also the cyclization to give compounds of type I, are described in European Patent No. 557 879.

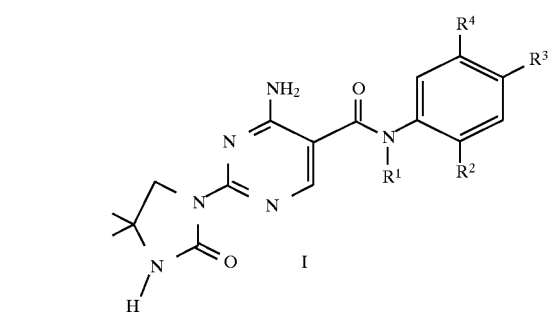

Process C for the preparation of the compounds of formula I comprises reacting a) ethyl 4-amino-2-(4,4-dimethylimidazolidin-2-on-1-yl)pyrimidine-carboxylate with 2,2-diethoxy-1-methylpyrrolidine in a suitable solvent, such as, for example, ethanol at a temperature from 0° to 150° C, to give ethyl 4-(1-methylpyrrolidin-2-ylideneamino) -2-(4,4-dimethyl-imidazolidin-2-on-1-yl) pyrimidine-5-carboxylate.

The ethyl 4-(1-methylpyrrolidin-2-ylideneamino)-2-(4,4-dimethyl-imidazolidin-2-on-1-yl)pyrimidine-5-carboxylate obtained in the first stage is reacted with NaI and TMSCl in a suitable solvent, such as, for example, acetonitrile, at a temperature from 0° to 150° C. to give 4-(l-methyl-pyrrolidin-2-ylideneamino)-2-(4,4-dimethylimidazolidin-2-on-1-yl)pyrimidine-5-carboxylic acid.

The 4-(l-methylpyrrolidin-2-ylideneamino)-2-(4,4-dimethylimidazolidin-2-on-1-yl)pyrimidine-5-carboxylic acid obtained in the second stage is reacted with a compound of the formula V, in which $R^1$, $R^2$, $R^3$ and $R^4$ have the meanings indicated for formula I. This is carried out in a suitable solvent, such as, for example, DMF at a temperature from 0° to 150° C. in the presence of TOTU and of an auxiliary base, such as, for example, triethylamine. The compound of the formula VI is obtained here.

The compound of the formula VI, in which $R^1$, $R^2$, $R^3$ and $R^4$ have the meanings indicated for formula I, obtained in the third stage is reacted with ethylenediamine in a suitable solvent, such as, for example, isopropanol at a temperature of 0°–150° C. in the presence of an auxiliary base, such as, for example, aqueous ammonia solution to give a compound of the formula I.

The 4-amino-2-(4,4-dimethylimidazolidin-2-on-1-yl) pyrimidine-5-carboxylic acid whose acid chloride forms the starting material of process A or whose ester forms the starting material of process C is prepared as follows:

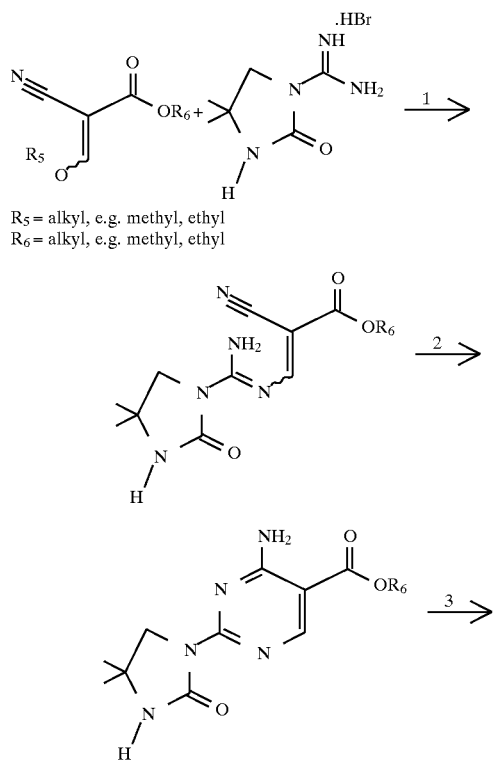

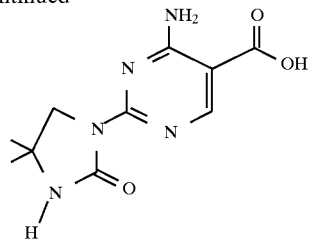

In the first stage, 1-amidino-4,4-dimethylimidazolidin-2-one hydrobromide and alkyl 2-cyano-3-alkoxyacrylate are reacted at a temperature from 0° to 150° C. in a suitable solvent, such as, for example, isopropanol, in the presence of base, such as, for example, KOH, to give alkyl 3-(1-amidino-4,4-dimethylimidazolidin-2-one)-2-cyanoacrylate.

In the second stage, alkyl 3-(1-amidino-4,4-dimethylimidazolidin-2-one)-2-cyanoacrylate is cyclized at a temperature from 0° to 150° C. in a suitable solvent, such as, for example, toluene, in the presence of trifluoroacetic acid or acetic acid to give alkyl 4-amino-2-(4,4-dimethylimidazolidin-2-on-1-yl)pyrimidine-5-carboxylate.

In the third stage, the alkyl 4-amino-2-(4,4-dimethylimidazolidin-2-on-1-yl)pyrimidine-5-carboxylate is hydrolyzed according to known methods to give 4-amino-2-(4,4-dimethylimidazolidin-2-on-1-yl)pyrimidine-5-carboxylic acid.

Pharmaceutical Preparations

The present invention also relates to pharmaceutical preparations which, in addition to nontoxic, inert pharmaceutically suitable excipients, contain one or more active compounds according to the invention or which consist of one or more active compounds according to the invention. The pharmaceutical preparations of the invention can also contain further pharmaceutical active compounds in addition to the active compounds according to the invention. The invention further relates to processes for the production of these pharmaceutical preparations.

Nontoxic inert pharmaceutically suitable excipients are understood as meaning pharmaceutically acceptable solid, semisolid or liquid diluents, fillers and formulation auxiliaries of any type, which after mixing with the active compound bring this into a form suitable for administration. Suitable administration forms of the compounds according to the invention are, for example, tablets, coated tablets, capsules, pills, aqueous solutions, suspensions and emulsions, if appropriate sterile injectable solutions, nonaqueous emulsions, suspensions and solutions, sprays and also preparation forms with protracted release of active compound.

The therapeutically active compounds should be present in the above-mentioned pharmaceutical preparations expediently in a concentration of approximately 0.1 to 99, preferably of 0.5 to 70, percent by weight of the total mixture. The administration concentrations for solutions and aerosols in the form of spray is in general 0.1 to 20, preferably 0.5–5, percent by weight. The active compounds or the pharmaceutical preparations of the invention can be administered orally, parenterally, intraperitoneally and/or rectally.

The above-mentioned pharmaceutical preparations are prepared in a customary manner according to known methods, e.g. by mixing the active compound(s) with the excipient(s).

The compounds of the present invention and their salts which are utilizable, for example, as hypolipidemics can be used for the production of pharmaceutical preparations which contain an effective amount of the active substance together with excipients and which are suitable for enteral and parenteral administration. Tablets or capsules (gelatin capsules) are preferably used which contain the active compound together with diluents or excipients, e.g., lactose, dextrose, cane sugar, mannitol, sorbitol, cellulose, various types of starch and/or glycerol, and lubricants such as silica, talc, stearic acid or its salts, such as magnesium or calcium stearate, and/or polyethylene glycol. Tablets also contain binders such as magnesium carbonate, magnesium aluminum silicate, starch, gelatin, tragacanth, methylcellulose, sodium carboxymethylcellulose and/or polyvinylpyrrolidone and, if required, colorants, flavorings and sweeteners. Injectable solutions are preferably isotonic aqueous solutions or suspensions, which can be sterilized and can contain auxiliaries, such as preservatives, stabilizers, wetting agents and/or emulsifiers, solubilizers, salts for regulating the osmotic pressure and/or buffer substances. The pharmaceutical preparations according to the invention, which if desired can contain further pharmacologically active substances, are prepared, for example, by means of conventional mixing, granulating and pan-coating processes, and contain 0.1% to preferably 80%, preferably approximately 5% to approximately 65%, of the active compound.

Oral administration takes place in pharmaceutically customary preparations, for example, in the form of tablets, coated tablets or capsules, which, for example, per daily dose contain 5 to 1000 mg, preferably 20 to 200 mg, of the active compound as a mixture with a customary excipient and/or constituent, it being possible to give individual doses of 5 to 200 mg, preferably once to three times daily.

It may, however, be necessary to deviate from the doses mentioned, namely depending on the nature and the body weight of the subject to be treated, the nature and severity of the disease, the type of preparation and of administration of the pharmaceutical, and the time or interval within which administration takes place. Thus in some cases it may be adequate to manage with less than the abovementioned amount of active compound, while in other cases the abovementioned amount of active compound has to be exceeded. The setting of the optimum dose and type of administration of the active compounds necessary in each case can easily be carried out by any person skilled in the art on the basis of his expert knowledge.

Pharmacological Activity

Owing to their stability in the metabolism, the compounds of the formula I and their physiologically tolerable salts are ideal pharmaceuticals for the treatment of disorders of lipid metabolism, in particular of hyperlipidemia. By affecting the LDL receptor, the compounds are particularly suitable for effectively lowering the plasma levels. The following results confirm the pharmacological activity of the compounds described.

Using a surrogate system, the present inventors sought to confirm the pharmacological activity of the inventive compounds. Thus, utilizing the human hepatocytoma cell line HepG2, which is recognized on all sides as a model, it was observed that the LDL receptor mRNA levels are increased by the compounds of the formula I (Table I). Even in rat livers, within a few hours the LDL receptor mRNA levels are increased by the compounds of the formula I (Table II). The observed stimulation is in the range from 170 to 350% of the controls (control=100%). Accordingly, an effective amount of an inventive compound can include an amount sufficient to increase CDL receptor levels or reduce plasma lipid levels.

The preparation of the mRNA was carried out according to the method of Chomczynski, P. and Sacchi, N., Anal. Biochem. 162, 156–159 (1987). In organs (such as, for example, liver), the deep-frozen tissue was homogenized on dry ice beforehand in a mortar, and the mRNA was further enriched by means of Oligo dT according to standard methods (cf. Sambrook, J., Fritsch, E. F. and Maniatis, T., Molecular Cloning, second Edition, Cold Spring Harbor (1989); in this collection of methods, there are also descriptions of all further relevant molecular biology standard methods used here). Five to 20 $\mu$m of the dissolved mRNA thus obtained were denatured according to standard methods and separated on 1% horizontal agarose gels. The mRNA was transferred to Hybond N membranes (Amersham) by means of capillary blot. The specific hybridization probe used was a partial LDL receptor cDNA clone and the internal standard a plasmid which contained a $\beta$-actin gene. Both plasmids were labeled by means of a random primer kit from Amersham up to a specific activity of $5 \times 10^9$ cpm/$\mu$g. Prehybridization, hybridization and washing of the filters were carried out by standard methods. The filters were then exposed at $-70°$ C. on Cronex 4 films (Dupont) overnight up to 14 days in the presence of an intensifying screen, and the hybridization signals were quantified using a commercial laser densitometer by means of the film-blackening intensity. The quotient of the intensity of the LDL receptor band and of the actin band was then determined as an internal standard to correct yield variations.

Table I presents the stimulation of the LDL receptor mRNA expression in HepG2 cells by selected compounds of formula I in whole serum (final concentration of the compounds $10^{-6}$M) after a 16 h incubation. The HepG2 cells were incubated with fetal calf serum (final concentration 10%) in RPMI 1640 standard medium. The induction control used was serum-free RPMI medium. The total mRNA was then prepared, and the relevant LDL receptor mRNA and $\beta$-actin mRNA levels were determined by means of the Northern blot technique. The quotient of the LDL receptor mRNA signal and the $\beta$-actin mRNA signal of the control (without substance addition) was set at 100%, and the stimulation of the LDL receptor mRNA level above it achieved under the influence of the compounds was expressed in percent of the control.

TABLE I

| Compounds according to Example | Concentration | LDL receptor mRNA |
| --- | --- | --- |
| 1 | $2 \times 10^{-6}$M | 220 |
| 10 | $2 \times 10^{-6}$M | 206 |
| 11 | $2 \times 10^{-6}$M | 290 |

Table II shows the stimulation of the LDL receptor mRNA expression in rat livers 6 hours after an administration of selected compounds of formula I (dose of 30 mg/kg). Liver tissue was removed and shock-frozen in liquid nitrogen. The mRNA was then isolated as described, and the relative LDL receptor mRNA levels were determined by means of the Northern blot technique. The mRNA levels of untreated control animals were set at 100%, and the stimulation of the LDL receptor mRNA in percent of the control was calculated.

TABLE II

| Compounds according to Example | Concentration | LDL receptor mRNA |
|---|---|---|
| 1 | 30 mg/kg | 220 |
| 2 | 30 mg/kg | 245 |
| 3 | 30 mg/kg | 200 |
| 6 | 30 mg/kg | 216 |
| 8 | 30 mg/kg | 182 |
| 9 | 30 mg/kg | 193 |
| 14 | 30 mg/kg | 194 |
| 17 | 30 mg/kg | 195 |

Metabolic Stability

It is known that compounds of formula I where $R^1$=alkyl are degraded in the metabolism to compounds of the formula I where $R^1$=H (in the following called compound A). Accordingly, the instant inventors sought to investigate the metabolic fate of our inventive compounds. The following experiments, which can be carried out using intact human hepatocytes or liver extracts, are used to investigate the dealkylation tendency of the compounds of the formula I according to the invention in comparison to 4-amino-2-(4,4-dimethyl-2-oxoimidazolidin-1-yl)pyrimidine-5-N-(ethyl)-N-(3-trifluoromethyl-phenyl)carboxamide hydrochloride (compound of Example 2 from EP 0 557 879—in the following called compound B).

Preparation of Human Hepatocytes

The human hepatocytes were prepared by the University of Pittsburgh, Pathology Division. Briefly, after perfusion of the livers, a cell suspension was prepared using William's E medium with addition of insulin (7M), dexamethasone (7M), penstrep and fungazone (Gibco). The suspension was streaked out in flasks; the medium was supplemented with 10% calf serum. After the exchange of the medium for serum-free William's E, the flasks were despatched at room temperature. After arrival, the medium was exchanged again. On vital testing with Trypan Blue, the cells showed a vitality of >95%. The time between the liver perfusion and the start of the incubations was about 48 hours. The cultures contained about $12 \times 10^6$ hepatocytes in 25 ml of culture medium.

Preparation of 9000 g Liver Fractions

Frozen samples of pieces of human liver stored at −78° C. were thawed by introducing them into a 1.1% strength potassium chloride solution at a temperature of 4° C. Such a freezing/thawing cycle does not adversely affect the metabolically relevant enzymes [P. J. Meier, H. K. Muller, B. Dick, U. A. Meyer; Gastroenterology 85, 682 (1983)]. After thawing, the pieces of liver were prepared by standard processes [A. Y. H. Lu, W. Levin; Biochem. Biophys. Res. Comm. 46, 1339–1344 (1972), P. G. Gervasi et al.; Xenobiotica 12/8, 517 (1982)]. The temperature was kept between 0° and 4° C. during the preparation. The 9000 g fractions of ten human livers were mixed in order to exclude interindividual enzyme differences.

The content of cytochrome P 450 of the 9000 g fractions was determined to be as follows [T. Omura, R. Sato; J. Biol. Chem. 239, 2370 (1964)]:

| Protein content | [mg/ml] |
|---|---|
| Man* | 22 |

*Mixture of liver samples from 10 persons

Assay Conditions

The test substances were dissolved in DMSO at a concentration of about 10 mg/ml. Aliquot parts of this solution were added under sterile conditions to the hepatocyte cultures or the 9000 g fractions. The incubations were carried out at 37° C. in an atmosphere having 5% $CO_2$ and >90% atmospheric humidity. The incubation time was 3 hours for the 9000 g fractions and 48 hours for the hepatocytes. NADPH and $Mg^{2+}$ were added to the 9000 g fractions as cofactors [P. G. Gervasi et al.; Xenobiotica 12/8, 517 (1982)]. All samples were frozen immediately after incubation and stored at below −20° C. until analysis.

The test substances were incubated at the appropriate concentrations in the buffer system for the 9000 g fractions and the hepatocyte culture medium in order to demonstrate the stability of the substance in the culture media. For each species and each time, all incubations with hepatocytes and 9000 g fractions were carried out without addition of a test substance. The samples obtained were used as controls in the chromatographic analysis.

For the quantitative determination of compound A, i.e. the $R^1$-dealkylated metabolite, in the in vitro incubation mixtures, 0.25 μl of each mixture was in each case diluted with 0.75 μl of bovine serum. These samples were analyzed by the following test for the determination of compound B free base and metabolite compound A free base in serum:

Fifty microliters of the prepared solution of an internal standard (10 μg of a compound of the formula I where $R^1$=$CH_3$, $R^2$, $R^3$=H and $R^4$=$CF_3$/ml of methanol), 0.1 ml of sodium acetate buffer (0.4M, pH 5.5) and 5 ml of ethyl ether were added to 0.1 ml of serum. The mixture was shaken for 20 min. After centrifuging, 4 ml of the organic phase were transferred, 3 ml of n-hexane were added and the mixture was extracted with 0.5 ml of 1% strength (v/v) aqueous trifluoroacetic acid. The upper organic layer was aspirated off and discarded. The aqueous residue was evaporated at 40° C. for 30 min. in order to remove residues of the organic solvent. 100 μl of the remaining aqueous phase were injected into the HPLC apparatus. HPLC analysis was carried out on a C18 RP column (TosoHaas Semi-Micro TSK gel ODS 80 TS) using a mobile phase of 800 g of water, 270 g of acetonitrile and 1 ml of trifluoroacetic acid. The flow rate was 0.2 ml/min. The quantitative determination of the analytes was carried out by measuring the peak heights with the aid of a UV detector at γ=240 nm. The calibration range was between 50 and 0.05 μg/ml corresponding to 200 to 0.2 μg/ml in the undiluted in vitro sample. The detection limit was 0.05 μg/ml corresponding to 0.2 μg/ml in the undiluted in vitro sample.

Additionally, unprepared samples were analyzed both with the aid of radio-detectors and UV detectors using the following HPLC system:

Column: Nucleosil 100 or 120 C 18.5 μm, 250×4[l.d.] mm (CTI GmbH, Idstein, Germany)

Eluent A: 0.1% by weight ammonium acetate in water

Eluent B: Eluent A/acetonitrile 1:4 (v/v)

| | | Gradient: | |
|---|---|---|---|
| Flow rate | Time [min] | % A [ml/min] | % B |
| 0 | 1.0 | 100 | 0 |
| 5 | 1.0 | 100 | 0 |
| 35 | 1.0 | 75 | 25 |
| 45 | 1.0 | 75 | 25 |
| 46 | 1.9 | 0 | 100 |
| 51 | 1.9 | 0 | 100 |
| 52 | 1.0 | 100 | 0 |
| 59 | 1.0 | 100 | 0 |

Detection Radiodetector Ramona 92 (Raytest, Straubenhardt, Germany) UV at 254 nm; detector model 204 (Linear Instruments, Reno, Nev., USA)

TABLE 1

| Compound | Incubation time [h] | relative content of compound A |
|---|---|---|
| Compound B | 0.5 | 4% |
| | 1 | 8% |
| | 2 | 10% |
| | 3 | 12% |
| Example 1 | 0.5 | <2% |
| | 1 | <2% |
| | 2 | 3% |
| | 3 | 4% |
| Example 2 | 0.5 | <2% |
| | 1 | <2% |
| | 2 | <2% |
| | 3 | <2% |
| Example 12 | 0.5 | 2% |
| | 1 | 4% |
| | 2 | 6% |
| | 3 | 9% |

Table 1 shows representative data obtained by the assay method. These data demonstrate that the compounds of formula I according to the invention have a greater stability than the comparison compound B.

The following examples further serve to illustrate the invention in greater detail without restricting same to products and embodiments described in the examples.

EXAMPLE 1

Using Process A to Synthesize Representative Compound 4-Amino-2-(4,4-dimethylimidazolidin-2-on-1-yl) pyrimidine-5-N-(2,2,2-trifluoroethyl)-N-[(3-trifluoromethyl)phenyl]carboxamide hydrochloride First Stage: Preparation of 4-amino-2-(4,4-dimethylimidazolidin-2-on-1-yl)-pyrimidine-5-N-(2,2,2-trifluoroethyl)-N-[(3-trifluoromethyl)phenyl] carboxamide Initially, 9.66 g of 4-amino-2-(4,4-dimethylimidazolidin-2-on-1-yl)-5-pyrimidine-carboxylic acid (0.038 mol) are suspended in 100 ml of dry DME, then 11.5 ml (161 mmol) of thionyl chloride are added dropwise with stirring at room temperature and the mixture is subsequently refluxed for 5 hours (85°–90° C.). To remove the excess thionyl chloride, 50 ml of DME are distilled off, in each case (repeated altogether 3×!) 50 ml of fresh absolute DME are added and 50 ml of DME are again distilled off. Subsequently, 50 ml of DME are added once more. A mixture of 11.2 g (0.046 mol) of N-(2,2,2-trifluoroethyl)-3-trifluoromethylaniline and 5.75 g (0.046 mol) of triethylamine is then added dropwise at 40° C. with stirring to the acid chloride suspension, slight warming occurring. The mixture is stirred at 60°–70° C. for 5 minutes, then a further 2.3 ml of triethylamine are added dropwise and the mixture is stirred at 80° C. for 30 minutes, and then allowed to stand overnight at room temperature. After this, 150 ml of H$_2$O are added dropwise (slight warming) and the DME is stripped off on a rotary evaporator. The acidic aqueous phase is extracted once with ethyl acetate, adjusted to pH 8–9 using 2N aqueous NaOH solution and extracted three more times with ethyl acetate. The combined extracts are dried using MgSO$_4$, filtered and concentrated. 4 g of crude product are obtained in foamy solid form. Purification is carried out by means of column chromatography using silica gel and ethyl acetate/methanol (10:1) as eluent. Thus 2.5 g of purified product are isolated as white crystals (13.8% of theory, based on carboxylic acid employed).

M.P.: 248° C.
M.S.: m/e 477.2 (M$^+$+1);
200 MHz $^1$H-NMR (DMSO-d$_6$, ppm):
1.2(s, 6H), 3.55(s, 2H), 4.75(q, 2H), 7.0(brs, 2H), 7.28 (s, 1H), 7.54–7.64 (m, 3H), 7.75–7.82 (m, 2H).

Second Stage: Preparation of 4-amino-2-(4, 4-dimethylimidazolidin-2-on-1-yl) -pyrimidine-5-N-(2,2,2-trifluoroethyl)-N-[(3-trifluoromethyl)-phenyl] carboxamide hydrochloride First, 2.5 g (0.005 mol) of 4-amino-2-(4,4-dimethylimidazolidin-2-on-1-yl)-pyrimidine-5-N-(2,2,2-trifluoroethyl)-N-[(3-trifluoromethyl)phenyl]-carboxamide are suspended in 60 ml of acetone. Next, 1 ml of a saturated ethereal HCl solution at 0° C. is added dropwise with stirring in an ice bath with exclusion of moisture. The mixture is additionally stirred in the cooling bath for 2 more hours and allowed to stand at room temperature overnight. Finally, 200 ml of ether are then added, the mixture is cooled to 0° C. after crystallization begins and the crystals are filtered off with suction.

Yield: 2.5 g of white crystals (93% of theory).
M.P.: >300° C.
200 MHz $^1$H-NMR (DMSO-d$_6$, ppm):
1.25(s, 6H), 3.6(s, 2H), 4.75(t, 2H), 7.58–7.72 (m, 3H), 7.95(s, 1H), 8.04(s, 1H), 8.62(s, 1H), 9.0(brs, 1H), 11,8–13.4(brs, 1H).

EXAMPLE 2

Using Process B to Produce Representative Compound 4-Amino-2-(4,4-dimethylimidazolidin-2-on-1-yl)pyrimidine-5-N-(2,2,3,3,4,4,4-heptafluorobutyl)-N-[(3-trifluoromethyl)phenyl] carboxamide hydrochloride First Stage: Preparation of Cyanoacetyl Chloride Initially, 30.6 g (1.375 mol) of cyanoacetic acid are dissolved in 420 ml of absolute ether in a 1 l four-necked flask and a total of 75 g of PCl$_5$ (0.36 mol) are added in portions with cooling in an ice bath. The mixture is then stirred at room temperature for 3 hours until the PCl$_5$ has dissolved completely and is concentrated in vacuo, and the residue is evaporated twice in vacuo with toluene to remove the POCl$_3$ formed. The residual red oil is employed immediately in the next reaction. (Preparation according to Org. Synth. (1973), Coll. Vol. V, page 171–173.)

Second Stage: Preparation of N-(2,2,3,3,4,4,4-heptafluorobutyl)-N-[(3-trifluoromethyl)phenyl] cyanoacetamide The cyanoacetyl chloride obtained in the preceding reaction is dissolved in 300 ml of absolute CH$_2$C$_2$ and introduced into a 1 l four-necked flask. 58 g (0.17 mol) of N-(2,2,3,3,4,4,4-heptafluorobutyl)-3-trifluoromethylaniline, dissolved in 150 ml of absolute CH$_2$C$_2$, and 23.5 ml (0.17 mol) of triethylamine are added dropwise, the reaction mixture coming to the boil. It is stirred at 40° C. for 1 more hour and then worked up: 150 ml of CH$_2$Cl$_2$ and 300 ml of H$_2$O are added and the phases are separated. The CH$_2$Cl$_2$ phase is washed 5× with water and the H$_2$O phase is extracted 1× with CH$_2$C$_2$. The combined CH$_2$Cl$_2$ phases are dried using MgSO$_4$ filtered and concentrated in vacuo. Thus, 70 g of a brown oily residue remain. For purification, flash column chromatography using 500 g of silica gel and n-heptane/ethyl acetate (1:1) as eluent is carried out. The chromatography affords 48.6 g of N-(2,2,3,3,4,4,4-heptafluorobutyl)-N-[(3-trifluoromethyl)phenyl] cyanoacetamide as a dark-yellow foam (~71% of theory).

MS: m/e 411.1 (M$^+$+1)

200 MHz $^1$H-NMR (DMSO-d$_6$, ppm):
3.44(s, 2H), 4.68(t, 2H), 7.65–7.95(m, 4H).

Third Stage: Preparation of ethoxymethylene-N-(2,2,3,3,4,4,4-hepta-fluorobutyl)-N-[(3-trifluoromethyl)phenyl]cyanoacetamide First, 48.5 g (0.118 mol) of N-(2,2,3,3,4,4,4-heptafluorobutyl)-N-[(3-trifluoro-methyl)phenyl] cyanoacetamide, 39.5 ml (0.237 mol) of triethyl orthoformate and 44.9 ml (0.475 mol) of acetic anhydride are mixed together at room temperature in a 250 ml four-necked flask provided with a column head and mechanical stirrer with a glass sleeve and the mixture is slowly heated in an oil bath. The reaction begins at a bath temperature of 145° C. About 60 ml are distilled off in the course of 1–2 hours. After this time, the reaction has ended (TLC checking). All volatile constituents are distilled off in vacuo at a pressure of 1 mm Hg and a bath temperature of 140° C. The residue which remains is treated with ethyl acetate, the mixture is concentrated on a rotary evaporator and the residue is evaporated once with toluene. The residual red-brown oil (56 g, about 100% of theory) is employed in the next stage without further purification.

M.S.: m/e 467.1 (M$^+$+1)

200 MHz $^1$H-NMR (DMSO-d$_6$, ppm):
1.22(t, 3H), 4.38(q, 2H), 4.78(t, 2H), 7.65–7.9 (m, 4H), 8.36(s, 1H).

Fourth stage: Preparation of 4-amino-2-(4,4-dimethylimidazolidin-2-on-1-yl)pyrimidine-5-N-(2,2,3,3,4,4,4-heptafluorobutyl)-N-[(3-trifluoromethyl)phenyl]carboxamide First, 22.5 g (0.187 mol) of 1-amidino-4,4-dimethylimidazolidin-2-one are introduced as a suspension in 300 ml of absolute DME with stirring and exclusion of moisture. Next, 56 g (0.119 mol) of ethoxymethylene-N-(2,2,3,3,4,4,4-heptafluorobutyl)-N-[(3-trifluoromethyl)phenyl] cyanoacetamide in 300 ml of absolute DME are slowly added dropwise at 0° C. After addition, the mixture is stirred at room temperature for 2 hours. After this time the reaction has ended (TLC checking). 125 ml of glacial acetic acid are added dropwise with stirring to this solution and it is stirred for 2 hours at a temperature of 50° C. After allowing to stand overnight at room temperature, the cyclization to the pyrimidine derivative has ended. For working-up, the precipitated 5-cyano-4-pyrimidone derivative formed as a by-product is filtered off. The filtrate is concentrated, the glacial acetic acid is evaporated with toluene, and the semisolid residue is taken up in ethyl acetate. Additionally precipitated amounts of the 5-cyano-4-pyrimidone derivative formed are removed again by filtration. The ethyl acetate phase is then washed 2× with 2N aqueous NaOH solution and 2× with saturated sodium chloride solution, dried using MgSO$_4$, filtered and concentrated on a rotary evaporator, after which, as a residue, 51 g of crude product remain as a dark oil. Purification is carried out by means of column chromatography using silica gel and ethyl acetate as eluent. After evaporating the solvent, 12.56 g of 4-amino-2-(4,4-dimethylimidazolidin-2-on-1-yl)pyrimidine-5-N-(2,2,3,3,4,4,4-heptafluorobutyl)-N-[(3-trifluoro- methyl)phenyl]carboxamide remain as yellowish crystals (18% of theory).

M.P.: 188° C.

M.S.: m/e 577.2 (M$^+$+1)

200 MHz $^1$H-NMR (DMSO-d$_6$, ppm):
1.2(s, 6H), 3.55(s, 2H), 4.8(t, 2H), 7.0(brs, 2H), 7.28 (s, 1H), 7.54–7.64 (m, 3H), 7.78–7.80 (m, 2H).

Fifth Stage: Preparation of 4-amino-2-(4,4-dimethylimidazolidin-2-on-1-yl)pyrimidine-5-N-(2,2,3,3,4,4,4-heptafluorobutyl)-N-[(3-(2,2,3,3,4,4,4-heptafluorobutyl)-N-[(3-trifluoromethyl)phenyl] carboxamide hydrochloride Initially, 12.5 g (0.023 mol) of 4-amino-2-(4,4-dimethylimidazolidin-2-on-1-yl)-pyrimidine-5-N-(2,2,3,3,4,4,4-heptafluorobutyl)-N-[(3-trifluoromethyl)phenyl] carboxamide are dissolved in 200 ml of acetone. After dissolution, 6 ml of a saturated ethereal HCl solution at 0° C. are added dropwise with stirring in an ice bath. The mixture is stirred for 2 more hours in a cooling bath with exclusion of moisture and allowed to stand at room temperature overnight. After this, 500 ml of ether are added, the mixture is cooled to 0° C. after crystallization begins and the crystals are filtered off with suction.

Yield: 10 g of slightly yellowish crystals (71% of theory).

M.P.: 278° C. (dec.).

200 MHz $^1$H-NMR (DMSO-d$_6$, ppm):
1.25 (s, 6H), 3.60 (s, 2H), 4.80 (t, 2H), 7.58–7.75 (m, 3H), 7.95 (s, 1H), 8.04 (s, 1H), 8.64 (s, 1H), 9.02 (brs, 1H), 11,60–13.20 (brs, 1H).

EXAMPLE 3

Preparation of 4-Amino-2-(4,4-dimethylimidazolidin-2-on-1-yl-pyrimidine-5-N-(2,2,3,3,3-pentafluoropropyl)-N-[(3trifluoromethyl)phenyl]carboxamide hydrochloride The compound is prepared analogously to Example 1, Process A.

Yield 10%

M.P.: >300° C.

M.S.: m/e=527.3 (M$^+$+1)

200 MHz $^1$H-NMR (DMSO-d$_6$, ppm):
1.30 (s, 6H), 3.60 (s, 2H), 4.80 (t, 2H), 7.60–7.80 (m, 3H), 7.95 (s, 1H), 8.05 (s, 1H), 8.60 (s, 1H), 8.70 (brs, 1H), 9.10 (brs 1H).

EXAMPLE 4

Preparation of 4-Amino-2-(4,4-dimethylimidazolidin-2-on-1-yl)pyrimidine-5-N-(2,2,3,3,4,4,4-heptafluorobutyl)-N-[(3-trifluoromethyl)phenyl]carboxamide hydrochloride The compound is prepared analogously to Example 1, Process A.

Yield: 12%

M.P.: 278° C. (dec.)

M.S.: m/e=577.2 (M$^+$+1)

200 MHz $^1$H-NMR (DMSO-d$_6$, ppm):
1.25 (s, 6H), 3.60 (s, 2H), 4.80 (t, 2H), 7.58–7.75 (m, 3H), 7.95 (s, 1H), 8.04 (s, 1H), 8.64 (s, 1H); 9.02 (brs, 1H), 11.60–13.20 (brs, 1H).

EXAMPLE 5

Preparation of 4-Amino-2-(4,4-dimethylimidazolidin-2-on-1-yl)pyrimidine-5-N-(2,2,2-trifluoroethyl)-N-[(3-trifluoromethoxy)phenyl] carboxamide The compound is prepared analogously to Example 1, Process A.

Yield: 1%
M.P.: 115° C.
M.S.: m/e 493.1 (M$^+$+1)
200 MHz $^1$H-NMR (DMSO-d$_6$, ppm):
 1.20 (s, 6H), 3.55 (s, 2H), 4.70 (t, 2H), 7.00 (brs, 2H), 7.20–7.40 (m, 4H), 7.40–7.50 (m, 1H), 7.80 (s, 1H).

EXAMPLE 6

Preparation of 4-Amino-2-(4,4-dimethylimidazolidin-2-on-1-yl)pyrimidine-5-N-(2,2,2-trifluoroethyl)-N-[(4-fluoro-3-trifluoromethyl) phenyl]carboxamide The compound is prepared analogously to Example 1, Process A.
Yield: 1%
M.P.: 90° C.
M.S.: m/e 495.2 (M$^+$+1)
200 MHz $^1$H-NMR (DMSO-d$_6$, ppm):
 1.30 (s, 6H), 3.60 (s, 2H), 4.70 (t, 2H), 7.00 (brs, 2H), 7.30 (s, 1H), 7.40–7.70 (m, 2H), 7.90 (m, 1H).

EXAMPLE 7

Preparation of 4-Amino-2-(4,4-dimethylimidazolidin-2-on-1-yl) pyrimidine-5-N-(2,2,3,3,3-pentafluoropropyl)-N-[(3-trifluoromethoxy)phenyl]carboxamide hydrochloride The compound is prepared analogously to Example 2, Process B.
Yield: 11%
M.P.: 287° C.
M.S.: m/e 543.1 (M$^+$+1)
200 MHz $^1$H-NMR (DMSO, ppm):
 1.25 (s, 6H), 3.60 (s, 2H), 4.80 (t, 2H), 7.35 (m, 1H), 7.50–7.60 (m, 3H), 8.00 (s, 1H), 8.50–9.20 (brs, 2H), 8.60 (s, 1H).

EXAMPLE 8

Preparation of 4-Amino-2-(4,4-dimethylimidazolidin-2-on-1-yl)pyrimidine-5-N-[(4-chloro-3-trifluoromethyl)phenyl]-N-(2,2,2-trifluoroethyl)carboxamide hydrochloride The compound is prepared analogously to Example 1, Process A.
Yield: 12%
M.P.: 268°–270° C.
M.S.: m/e 511.5 (M$^+$+1)
200 MHz $^1$H-NMR (DMSO-d$_6$, ppm):
 1.20 (s, 6H), 3.55 (s, 2H), 4.75 (q, 2H), 7.05 (brs, 2H), 7.30 (s, 1H), 7.55 (dd, 1H), 7.70 (d, 1H), 7.90 (s, 1H), 7.95 (d, 1H).

EXAMPLE 9

Preparation of 4-Amino-2-(4,4-dimethylimidazolidin-2-on-1-yl)pyrimidine-5-N-[(4-chloro-3-trifluoromethyl)phenyl]-N-(2,2,3,3,3-pentafluoropropyl)carboxamide The compound is prepared analogously to Example 2, Process B.
Yield: 12%
M.P.: 232°–234° C.
M.S.: m/e 561.8 (M$^+$1)
200 MHz $^1$H-NMR (DMSO-d$_6$, ppm):
 1.20 (s, 6H), 3.55 (s, 2H), 4.80 (t, 2H), 7.00 (brs, 2H), 7.30 (s, 1H), 7.55 (dd, 1H), 7.70 (d, 1H), 7.90 (s, 1H), 7.95 (d, 1H).

EXAMPLE 10

Preparation of 4-Amino-2-(4,4-dimethylimidazolidin-2-on-1-yl)pyrimidine-5-N-[(4-chloro-3-trifluoromethyl) phenyl]-N-(2,2,3,3,4,4,4-heptafluorobutyl)carboxamide The compound is prepared analogously to Example 2, Process B.
Yield: 10%
M.P.: 228°–230° C.
M.S.: m/e 611.6 (M$^+$+1)
200 MHz $^1$H-NMR (DMSO-d$_6$, ppm):
 1.20 (s, 6H), 3.55 (s, 2H), 4.80 (t, 2H), 7.05 (brs, 2H), 7.30 (s, 1H), 7.55 (dd, 1H), 7.70 (d, 1H), 7.90 (s, 1H), 7.95 (d, 1H).

EXAMPLE 11

Preparation of 4-Amino-2-(4,4-dimethylimidazolidin-2-on-1-yl)pyrimidine-5-N-[(6-chloro-3-trifluoromethyl) phenyl]-N-(2,2,3,3,3-pentafluoropropyl)carboxamide hydrochloride The compound is prepared analogously to Example 1, Process A.
Yield: 29%
M.P.: 152° C.
M.S.: m/e 561.5 (M$^+$+1)
200 MHz $^1$H-NMR (DMSO-d$_6$, ppm):
 1.20 (s, 6H), 3.55 (s, 2H), 4.75 (t, 2H), 7.10 (brs, 2H), 7.35 (s, 1H), 7.70 (s, 2H), 7.75 (s, 1H), 8.30 (s, 1H).

EXAMPLE 12

Preparation of 4-Amino-2-(4,4-dimethylimidazolidin-2-on-1-yl)pyrimidine-5-[N-(3-trifluoromethylphenyl)-N-(2-fluoroethyl)]carboxamide The compound is prepared analogously to Example 1, Process A.
Yield: 51%
M.P.: 210° C.
M.S.: m/e 441 (M$^+$1)
200 MHz $^1$H-NMR (DMSO, ppm):
 1.30 (s, 6H), 3.75 (s, 2H), 4.15 (dt, 2H), 4.70 (dt, 2H), 6.40 (brs, 2H), 7.20–7.30 (m, 2H), 7.35–7.55 (m, 3H), 7.75 (s, 1H).

EXAMPLE 13

Preparation of 4-Amino-2-(4,4-dimethylimidazolidin-2-on-1-yl) pyrimidine-5-[N-(2,2,2-trifluoroethyl)-N-(3-trifluoromethyl-6-chlorophenyl)]carboxamide The compound is prepared analogously to Example 2, Process B.
Yield: 21%

M.P.: 222° C.

M.S.: m/e 511. (M$^+$+1)

200 MHz $^1$H-NMR (DMSO-d$_6$, ppm):
1.22 (s, 6H), 3.60 (s, 2H), 4.46 and 4.70 (2 x brs, 2H), 7.82 (m, 2H), 7.94 (s, 1H), 8.23 (s, 1H), 8.63 (s, 1H), 8.70 (brs, 2H).

EXAMPLE 14

Preparation of 4-Amino-2-(4,4-dimethylimidazolidin-2-on-1-yl)pyrimidine-5-[N-(3-trifluoromethyl-6-chlorophenyl)-N-(2,2,3,3,4,4,4-heptafluorobutyl)]-carboxamide The compound is prepared analogously to Example 2, Process B.

Yield: 9%.

M.P.: 203° C.;

M.S.: m/e 611.6 (M$^+$+1);

200 MHz $^1$H-NMR (DMSO-d$_6$, ppm):
1.20 (s, 6H), 3.55 (s, 2H), 4.78 (t, 2H), 7.08 (brs, 2H), 7.33 (s, 1H), 7.73 (s, 2H), 7.78 (s, 1H), 8.34 (s, 1H).

EXAMPLE 15

Preparation of 4-Amino-2-(4,4-dimethylimidazolidin-2-on-1-yl)pyrimidine-5-[N - (3-trifluoromethylphenyl)-N-(2,2,3,3,4,4,5,5,5-nonafluoropentyl)]carboxamide The compound is prepared analogously to Example 2, Process B.

Yield: 15%.

M.P.: 174°–176° C.

M.S.: m/e 627 (M$^+$+1)

200 MHz $^1$H-NMR (DMSO-d$_6$, ppm):
1.20 (s, 6H), 3.55 (s, 2H), 4.82 (t, 2H), 7.03 (brs, 2H), 7.28 (s, 1H), 7.55–7.70 (m, 3H), 7.80 (s, 2H).

EXAMPLE 16

Using Process C to synthesize representative compound 4-Amino-2-(4,4-dimethylimidazolidin-2-on-1-yl)pyrimidine-5-[N-(3-trifluoromethylphenyl)-N-(2,2,2-trifluoroethyl)]carboxamide First Stage: Synthesis of ethyl 4-(1-methylpyrrolidin-2-ylideneamino)-2-(4,4-dimethyl-2-imidazolidin-2-on-1-yl)pyrimidine-5-carboxylate Initially, 1 g (3.58 mmol) of ethyl 4-amino-2-(4,4-dimethylimidazolidin-2-on-1-yl)- pyrimidine-5-carboxylate are dissolved in 20 ml of ethanol, and the solution is treated with 10 ml of 2,2-diethoxy-1-methylpyrrolidine and stirred at room temperature for 1 h. After this, the solvent and excess NMP diethyl acetal are distilled off on a rotary evaporator, and the residue is stirred with diethyl ether and filtered off with suction. The residue is dissolved in hot EtOH, and the solution is boiled with active carbon, filtered and concentrated. 1.12 g of ethyl 4-(1-methylpyrrolidin-2-ylideneamino)-2-(4,4-dimethyl-2-oxo-1-imidazolidin-2-on-1-yl)pyrimidine-5-carboxylate are obtained.

Yield: 86.9%.

M.P.: 169° C.

M.S.: m/e 361.2 (M$^+$+1)

$^1$H NMR (200 MHz, DMSO-d$_6$, ppm), d [ppm]:
8.55 (s,1H), 7.35 (s,1H), 4.2 (q,2H), 3.73 (s,2H), 3.48 (t,2H), 3.03 (t,2H), 3.0 (s,3H), 1.98 (p,2H), 1.28 (t(masked)+s, 9H)

Second Stage: Synthesis of 4-(1-methylpyrrolidin-2-ylideneamino) -2-(4,4-dimethylimidazolidin-2-on-1-yl)pyrimidine-5-carboxylic acid First, 4 g (11.1 mmol) of 4-(1-methylpyrrolidin-2-ylideneamino)-2-(4,4-dimethylimidazolidin-2-on-1-yl) pyrimidine-5-carboxylate are dissolved (argon) in 100 ml of dry CH$_3$CN with 5.0 g (33.3 mmol) of dry NaI. The solution is heated to reflux, and 4.25 ml (3.64 g=33.3 mmol) of TMSCl are slowly added dropwise. The reaction mixture is boiled under reflux for 55 h. After this, a further equivalent of NaI and TMSCl is added and the mixture is heated for a further 15 h. The cooled reaction mixture is filtered with suction and the solid is washed with CH$_3$CN. The residue is stirred in water, filtered off with suction again, washed with a little ethanol and diethyl ether and dried in vacuo. Thus, 2.52 g of a colorless powder are obtained.

Yield: 68.3%.

M.S.: m/e 333.1 (M$^+$+1)

M.P.: 298° C. (dec.)

$^1$H NMR (200 MHz, DMSO-d$_6$, ppm), d [ppm]:
14.4 (s,broad, 1H), 8.88 (s,1H), 8.15 (s,1H), 3.83 (t+s, 4H), 3.6 (t,2H), 3.23 (s,3H), 2.18 (p,2H), 1.33 (s,6H)

Next, 1 g (3.98 mmol) of 4-amino-(2-(4,4-dimethylimidazolidin-2-on-1-yl)pyrimidine-5-carboxylic acid are suspended in a mixture of 20 ml of dry pyridine and 10 ml of NMP diethyl acetal and the mixture is stirred at room temperature for 48–72 h. A red-brown solution is soon obtained. The solution is diluted with about 50 ml of dichloromethane, treated with about 50 ml of water and then treated with glacial acetic acid with stirring. In this process, a yellowish precipitate separates in the interlayer between organic and aqueous phase. This precipitate is filtered off with suction, washed with water and then with ethanol and dried. Thus, 0.35 g of a colorless powder is obtained.

Yield: 26.5%

M.P.: dec. from 295° C.

Next, 5 g (19.9 mmol) of 4-amino-2-(4,4-dimethylimidazolidin-2-on-1-yl)-pyrimidine-5-carboxylic acid are suspended with stirring in 50 ml of dry dichloromethane. Subsequently, 10 ml of NMP diethyl acetal (2) are added (slight warming of the reaction mixture) and the suspension is stirred at room temperature for 24–48 h. The yellowish suspension is filtered off with suction and the residue is washed with dichloromethane. Thus, 2.07 g of a colorless powder are obtained.

Yield: 31.3%

M.P.: decomposition from 295° C.

$^1$H NMR 200 MHz, DMSO-d$_6$, ppm), d [ppm]:
14.4 (s,broad, 1H), 8.88 (s,1H), 8.15 (s,1H), 3.83 (t+s, 4H), 3.6 (t,2H), 3.23 (s,3H), 2.18 (p,2H), 1.33 (s,6H)

Third Stage: Synthesis of 4-(1-methylpyrrolidin-2-ylideneamino)-2-(4,4-dimethylimidazolidin-2-on-1-yl)pyrimidine-5-N-(2,2,2-trifluoroethyl)-N-[(3-trifluoromethyl)phenyl]carboxamide First, 1 g (3 mmol) of 4-(1-methylpyrrolidin-2-ylideneamino)-2-(4,4-dimethyl-imidazolidin-2-on-1-yl) pyrimidine-5-carboxylic acid and 0.73 g (3 mmol) of N-(2,2,2-trifluoroethyl)-3-trifluoromethylaniline are suspended in 20 ml of dry DMF at 0° C. and treated with stirring with 0.99 g (3 mmol) of TOTU (O-{[cyano(ethoxycarbonyl) methylidene]amino}-1,1,3,3-tetramethyluronium tetrafluoroborate) and 0.416 ml of NEt$_3$ (3 mmol). The mixture is stirred for 10' at 0° C. and allowed to warm to room temperature, a further 0.416 ml (3 mmol) of NEt$_3$ are additionally added after 1 h and the reaction mixture is then stirred overnight at a bath temperature of 100° C. The reaction solution is concentrated, and the residue is stirred with diethyl ether and filtered off with suction. The residue is stirred with saturated sodium carbonate solution and the aqueous phase is extracted several times with ethyl acetate. The ethyl acetate phase is concentrated and the residue is chromatographed on silica gel using ethyl acetate/methanol 9/1. Thus, 0.47 g of the anilide is obtained as an oil.

Yield: 28.4%

M.S.: m/e 558 (M$^+$+1)

$^1$H NMR (200 MHz, DMSO-d$_6$), d [ppm]:
  8.22 (s,1H), 7.66 (s,1H), 7.59–7.45 (m,3), 4.8 q,2H), 3.58 (s,2H), 3.42 (t,2H), 3.0 (s,3H), 2.2 (t,2H), 1.91 (p,2H), 1.22 (s,6H)

Fourth Stage: Synthesis of 4-amino-2-(4,4-dimethylimidazolidin-2-on-1-yl)-pyrimidine-5-[N-(3-trifluoromethylphenyl)-N-(2,2,2-trifluoroethyl)]carboxamide Initially, 84 mg (0.15 mmol) of 4-(1-methylpyrrolidin-2-ylideneamino)-2-(4,4-dimethylimidazolidin-2-on-1-yl)pyrimidine-5-N-2,2,2-trifluoroethyl)]-N-(3-trifluoromethylphenyl)carboxamide are suspended in a mixture of 5 ml of isopropanol with 3 ml of concentrated aqueous ammonia solution, and the mixture is treated with 3 drops of ethylenediamine and boiled under reflux for 24–48 h. The reaction solution is concentrated and chromatographed on silica gel using a mixture of EA/MeOH 9/1. A colorless oil is obtained, which crystallizes in an ice bath on addition of diethyl ether. Thus, 0.3 g of 4-amino-2-(4,4-dimethylimidazolidin-2-on-1-yl)pyrimidine-5-[N-(3-trifluoromethylphenyl)-N-(2,2,2-trifluoro-ethyl)]carboxamide are obtained as colorless crystals.

Yield: 44.7%

M.P.: 248° C.

$^1$H NMR (DMSO-d$_6$, ppm):
  1.2 (s,6H), 3.55 (s,2H), 4.75 (q,2H), 7.0 (s,broad,2H), 7.28 (s,1H), 7.64-7.54 (m,3H), 7.82-7.75 (m,2H)

EXAMPLE 17

Preparation of 4-Amino-2-(4,4-dimethylimidazolidin-2-on-1-yl)-5-pyrimidine-5-[N-(3-trifluoromethyl-4-fluorophenyl)-N-(2,2,3,3,4,4,4-heptafluorobutyl)]-carboxamide The compound was prepared analogously to Example 1, process A.

Yield 5%

M.P.: 128° C. (dec.)

M.S.: m/e=595.3 (M$^+$+1)

200 MHz $^1$H-NMR (DMSO-d$_6$, ppm):
  1.20 (s, 6H), 3.60 (s, 2H), 4.78 (t, 2H), 7.0 (brs, 2H), 7.20 (s, 1H), 7.42–7.95 (m, 3H).

EXAMPLE 18

Preparation of 4-Amino-2-(4,4-dimethylimidazolidin-2-on-1-yl)pyrimidine-5-[N-(2-fluoro-5-trifluoromethylphenyl)-N-(2,2,2-trifluoroethyl)]carboxamide hydrochloride The compound is prepared analogously to Example 2.

Yield 15%

M.P.: 295° C. (dec.)

M.S.: m/e=495.1 (M$^+$+1)

200 MHz $^1$H-NMR (DMSO-d$_6$, ppm):
  1.30 (s, 6H), 3.60 (s, 2H), 4.60–4.90 (brs, 2H), 7.55 (m, 1H), 7.85 (m, 1H), 7.95 (s, 1H), 8.25 (m, 1H), 8.60 (brs, 1H), 8.65 (s, 1H), 9.15 (brs, 1H).

EXAMPLE 19

Preparation of 4-Amino-2-(4,4-dimethylimidazolidin-2-on-1-yl)pyrimidine-5-[N-(2-fluoro-5-trifluoromethylphenyl)-N-(2,2,3,3-pentafluoropropyl)]carboxamide The compound is prepared analogously to Example 2.

Yield: 10%

M.P.: 240° C. (dec.)

M.S.: m/e=545.2 (M$^+$+1)

200 MHz $^1$H-NMR (DMSO-d$_6$, ppm):
  1.30 (s, 6H), 3.60 (s, 2H), 4.80 (t, 2H), 7.00 (brs, 2H), 7.35 (s, 1H), 7.45 (m, 1H), 7.75 (m, 1H), 7.80 (s, 1H), 8.25 (m, 1H).

EXAMPLE 20

Preparation of 4-Amino-2-(4,4-dimethylimidazolidin-2-on-1-yl)pyrimidine-5-(N-pentafluoropropyl-N-3-trifluoromethyl-4-fluorocarboxanilide)

The compound is prepared analogously to Example 2, process B.

Yield: 5%

M.P.: 208° C.

M.S.: m/e 545 (M$^+$+1)

200 MHz $^1$H-NMR (DMSO-d$_6$, ppm):
  7.95-7.85 (s, 2H), 7.70-7.45 (m, 2H), 7.3 (s, 1H), 7.0 (s, 2H), 4.78 (t, 2H), 3.58 (s, 2H), 4.78 (t, 2H), 3.58 (s, 2H), 1.20 (s, 6H)

EXAMPLE 21

Preparation of 4-Amino-2-(4,4-dimethylimidazolidin-2-on-1-yl)pyrimidine-5-(N-heptafluoropropyl-N-3-trifluoromethyl-6-fluorocarboxanilide)

The compound is prepared analogously to Example 2, process B.

Yield: 4%

M.P.: 200° C.

M.S.: m/e 595 (M$^+$1)

200 MHz $^1$H-NMR (DMSO-d$_6$, ppm):
  8.25 (d, 1H), 7.82 (s, 1H), 7.82-7.70 (m,1H), 7.45 (t, 1H), 7.32 (s, 1H), 7.05 (s, 2H), 4.8 (t, 2H), 3.58 (s, 2H), 1.20 (s, 6H).

EXAMPLE 22

Preparation of 4-Amino-2-(4,4-dimethylimidazolidin-2-on-2-yl)pyrimidine-5-N-[(3-trifluoromethylphenyl)-N-(2-fluoroethyl)]carboxamide First Stage: Preparation of ethyl 3-(1-amidino-4,4-dimethylimidazolidin-2-on-1-yl)-2-cyanoacrylate First, 2.11 g (37 mmol) of potassium hydroxide are dissolved in 30 ml of isopropanol with warming to 70° C.

After cooling to RT, 8.9 g (37 mmol) of 1-amidino-4,4-dimethylimidazolidin-2-one are added and the mixture is stirred for one more hour. 6.34 g (37 mmol) of ethyl 2-cyano-3-ethoxyacrylate, dissolved in 8 ml of isopropanol, are now added. The white suspension becomes more highly liquid for a while during the course of this, then the product begins to precipitate. The mixture is stirred for one more hour at 10° C., the precipitate is filtered off with suction and the product thus obtained is purified by washing with isopropanol, water, isopropanol and MTB ether. It is then dried to constant weight at 40° C. in vacuo.

Yield: 8.9 g (86% of theory)

M.S.: m/e=280.3 (M$^+$+1)

200 MHz $^1$H-NMR (DMSO-d$_6$, ppm):
1.25(t, 3H), 1.30(s, 6H), 3.70(s, 2H), 4.15(q, 2H), 8.25(s, 1H), 8.60(s, 1H), 8.75(brs, 2H).

Second Stage: Preparation of ethyl 4-amino-2-(4,4-dimethylimidazolidin-2-on-1-yl)pyrimidine-5-carboxylate First, 7.1 g (25 mmol) of the 3-(1-amidino-4,4-dimethylimidazolidin-2-on-1-yl)-2-cyanoacrylate prepared according to stage 1 are suspended in 30 ml of toluene. The suspension is treated with 2.9 g of trifluoroacetic acid and warmed to 95° C. After cyclization has ended, the mixture is cooled to RT and treated with 30 ml of MTB ether. The crude product thus obtained is purified by column chromatography on silica gel.

Yield: 5.05 g (72% of theory)

M.S.: m/e=280.2 (M$^+$+1)

200 MHz $^1$H-NMR (DMSO-d$_6$, ppm):
1.25(s, 6H), 1.30(t, 3H), 3.70(s, 2H), 4.15(q, 2H), 7.40(s, 1H), 7.55(brs, 1H), 7.75(brs, 1H), 8.60(s, 1H).

Third Stage: Preparation of 4-amino-2-(4,4-dimethylimidazolidin-2-on-1-yl)-pyrimidine-5-carboxylic acid First, 5.5 g (19.7 mmol) of the ethyl 4-amino-2-(4,4-dimethylimidazolidin-2-on-1-yl)-(pyrimidine-5-carboxylate prepared according to stage 2 are added to a solution of 0.8 g of sodium hydroxide in 55 ml of water. The suspension is warmed to 70° C. and stirred at this temperature until the starting material has disappeared (HPLC checking). It is now cooled to 50° C. and treated with approximately 2 ml of 37% HCl. During the course of this a white precipitate is deposited. The mixture is cooled in an ice bath and the precipitate is then filtered off with suction. Washing of the filter residue with ice-water and drying in vacuo yields clean product.

Yield: 3.30 g (66% of theory)

M.S.: m/e=280.2 (M$^+$+1)

200 MHz $^1$H-NMR (DMSO-d$_6$, ppm):
1.25(s, 6H), 1.30(t, 3H), 3.70(s, 2H), 4.15(q, 2H), 7.40(s, 1H), 7.55(brs, 1H), 7.75(brs, 1H), 8.60(s, 1H).

Abbreviations

The abbreviations used in the description have the following meanings:

DME Dimethoxyethane
NEt$_3$ Triethylamine
TMSCl Trimethylchlorosilane
LDL low-density lipoprotein
h hour
NMP N-Methylpyrrolidone
DMF Dimethylformamide
TOTU o-[(Cyano(ethoxycarbonyl)methylidene)amino-1,1,3,3-tetramethyl]uronium tetrafluoroborate The entire content of German Patent Application No. 196 25 088.9, filed Jun. 24, 1996, is hereby incorporated by reference.

The present invention has been described with reference to certain preferred embodiments thereof. It is to be understood that the invention is not to be limited in any way be these exemplary embodiments but rather is to be defined by the scope of the appended claims.

We claim:

1. A tertiary 4-amino-2-ureidopyrimidine-5-carboxamide compound of formula I

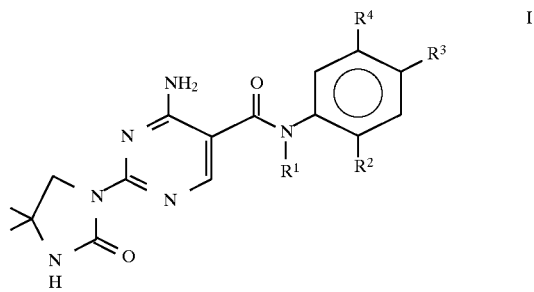

wherein

R$^1$ is (C$_1$–C$_8$)-alkyl wherein one or more or all hydrogens are replaced by fluorine, R$^2$ is selected from the group consisting of fluorine, chlorine, bromine, hydrogen, —O—(C$_1$–C$_8$)-alkyl and (C$_1$–C$_8$)-alkyl, wherein one or more or all of the hydrogens of the alkyl radical optionally are replaced by fluorine, R$^3$ is selected from the group consisting of fluorine, chlorine, bromine, hydrogen, —O—(C$_1$–C$_4$)-alkyl and (C$_1$–C$_4$)-alkyl, wherein one or more or all of the hydrogens of the alkyl radical optionally are replaced by fluorine, R$^4$ is CF$_3$ or OCF$_3$, or a physiologically tolerable acid addition salt thereof.

2. A compound according to claim 1, wherein:

R$^1$ is (C$_1$–C$_4$)-alkyl wherein one or more or all hydrogens are replaced by fluorine, R$^2$ is selected from the group consisting of fluorine, chlorine, hydrogen, —O—(C$_1$–C$_4$)-alkyl, and (c$_1$–C$_4$)-alkyl, wherein one or more or all of the hydrogens of the alkyl radical optionally are replaced by fluorine, R$^3$ is selected from the group consisting of fluorine, chlorine, bromine, hydrogen, —O—(C$_1$–C$_4$)-alkyl and (C$_1$–C$_4$)-alkyl, wherein one or more or all of the hydrogens of the alkyl radical optionally are replaced by fluorine, R$^4$ is CF$_3$, or OCF$_3$, or a physiologically tolerable acid addition salt thereof.

3. A compound according to claim 1, wherein:

R$^1$ is selected from the group consisting of trifluoromethyl, 2,2,2-trifluoroethyl, 2,2,3,3,3-pentafluoropropyl and 2,2,3,3,3,4,4,4-heptafluorobutyl;

R$^2$ is selected from the group consisting of fluorine, chlorine, hydrogen, —CF$_3$ and —OCF$_3$;

R$^3$ is selected from the group consisting of fluorine, chlorine, hydrogen, —CF$_3$ and —OCF$_3$; and R⁴ is CF₃,
or a physiologically tolerable acid addition salt thereof.

4. The compound according to claim 1, wherein the compound is selected from the group consisting of 4-Amino-2-(4,4-dimethylimidazolidin-2-on-1-yl) pyrimidine-5-N-(2,2,2-trifluoroethyl)-N-[(3-trifluoromethyl)phenyl]carboxamide hydrochloride, 4-Amino-2-(4,4-dimethylimidazolidin-2-on-1-yl) pyrimidine-5-N-(2,2,3,3,4,4,4-heptafluorobutyl)-N-[(3-trifluoromethyl)phenyl]carboxamide hydrochloride, 4-Amino-2-(4,4-dimethylimidazolidin-2-on-1-yl) pyrimidine-5-N-(2,2,3,3,3-pentafluoropropyl)-N-[(3-trifluoromethyl)phenyl]carboxamide hydrochloride, 4-Amino-2-(4,4-dimethylimidazolidin-2-on-1-yl) pyrimidine-5-N-(2,2,3,3,4,4,4-heptafluorobutyl)-N-[(3-trifluoromethyl)phenyl]carboxamide hydrochloride, 4-Amino-2-(4,4-dimethylimidazolidin-2-on-1-yl) pyrimidine-5-N-(2,2,2-trifluoroethyl)-N-[(3-trifluoromethoxy)phenyl]carboxamide, 4-Amino-2-(4,4-dimethylimidazolidin-2-on-1-yl)pyrimidine-5-N-(2,2,2-trifluoroethyl)-N-[(4-fluoro-3-trifluoromethyl)phenyl]carboxamide, 4-Amino-2-(4,4-dimethylimidazolidin-2-on-1-yl)pyrimidine-5-N-(2,2,3,3,3-pentafluoropropyl)-N-[(3-trifluoromethoxy)phenyl]carboxamide hydrochloride, 4-Amino-2-(4,4-dimethylimidazolidin-2-on-1-yl) pyrimidine-5-N-[(4-chloro-3-trifluoromethyl)phenyl]-N-(2,2,2-trifluoroethyl)carboxamide hydrochloride, 4-Amino-2-(4,4-dimethylimidazolidin-2-on-1-yl) pyrimidine-5-N-[(4-chloro-3-trifluoromethyl)phenyl]-N-(2,2,3,3,3-pentafluoropropyl)carboxamide, 4-Amino-2-(4,4-dimethylimidazolidin-2-on-1-yl)pyrimidine-5-N-[(4-chloro-3-trifluoromethyl)phenyl]-N-(2,2,3,3,4,4,4-heptafluorobutyl)carboxamide, 4-Amino-2-(4,4-dimethylimidazolidin-2-on-1-yl)pyrimidine-5-N-[(6-chloro-3-trifluoromethyl)phenyl]-N-(2,2,3,3,3-pentafluoropropyl)carboxamide hydrochloride, 4-Amino-2-(4,4-dimethylimidazolidin-2-on-1-yl)pyrimidine-5-[N-(3-trifluoromethylphenyl)-N-(2-fluoroethyl)]carboxamide, 4-Amino-2-(4,4-dimethylimidazolidin-2-on-1-yl) pyrimidine-5-[N-(2,2,2-trifluoroethyl)-N-(3-trifluoromethyl-6-chlorophenyl)]carboxamide, 4-Amino-2-(4,4-dimethylimidazolidin-2-on-1-yl)pyrimidine-5-[N-(3-trifluoromethyl-6-chlorophenyl)-N-(2,2,3,3,4,4,4-heptafluorobutyl)]carboxamide, 4-Amino-2-(4,4-dimethylimidazolidin-2-on-1-yl)pyrimidine-5-[N-(3-trifluoromethylphenyl)-N-(2,2,3,3,4,4,5,5,5-nonafluoropentyl)]carboxamide, 4-Amino-2-(4,4-dimethylimidazolidin-2-on-1-yl)pyrimidine-5-[N-(3-trifluoromethylphenyl)-N-(2,2,2-trifluoroethyl)]carboxamide, 4-Amino-2-(4,4-dimethylimidazolidin-2-on-1-yl)-5-pyrimidine-5-[N-(3-trifluoromethyl-4-fluorophenyl)-N-(2,2,3,3,4,4,4-heptafluorobutyl)]-carboxamide, 4-Amino-2-(4,4-dimethylimidazolidin-2-on-1-yl) pyrimidine-5-[N-(2-fluoro-5-trifluoromethylphenyl)-N-(2,2,2-trifluoroethyl)]carboxamide hydrochloride, 4-Amino-2-(4, 4-dimethylimidazolidin-2-on-1-yl)pyrimidine-5-[N-(2-fluoro-5-trifluoromethylphenyl)-N-(2,2,3,3-3-pentafluoropropyl)]carboxamide, 4-Amino-2-(4,4-dimethylimidazolidin-2-on-1-yl) pyrimidine-5-(N-pentafluoropropyl-N-3-trifluoromethyl-4-fluorocarboxanilide), 4-Amino-2-(4,4-dimethylimidazolidin-2-on-1-yl) pyrimidine-5-(N-heptafluoropropyl-N-3-trifluoromethyl-6-fluorocarboxanilide), 4-Amino-2-(4,4-dimethylimidazolidin-2-on-2-yl)pyrimidine-5-N-[(3-trifluoromethylphenyl)-N-(2-fluoroethyl)]carboxamide, and physiologically tolerable salts thereof.

5. A process of preparing a compound of claim 1, comprising

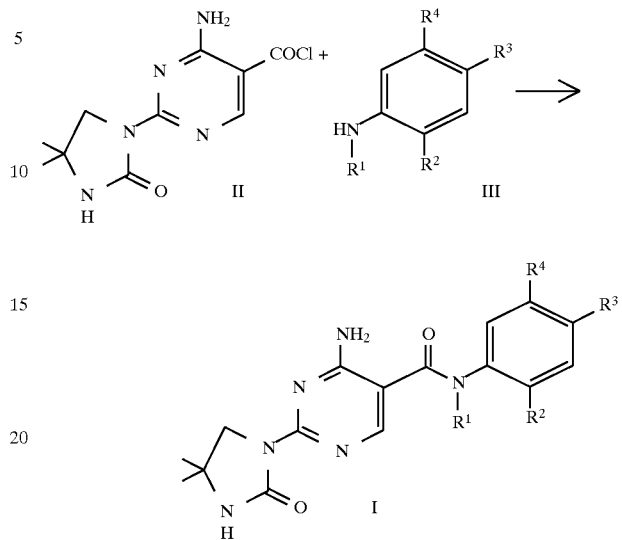

reacting a compound of formula II with a compound of formula III, wherein R¹, R², R³ and R⁴ are defined as in claim 1, at a temperature from 0° C. to 200° C. in a suitable solvent to give a compound of the formula I, and optionally converting the compound of the formula I obtained into a physiologically tolerable salt or converting a salt obtained into a physiologically tolerable salt.

6. A process of preparing the compounds of claim 1, comprising

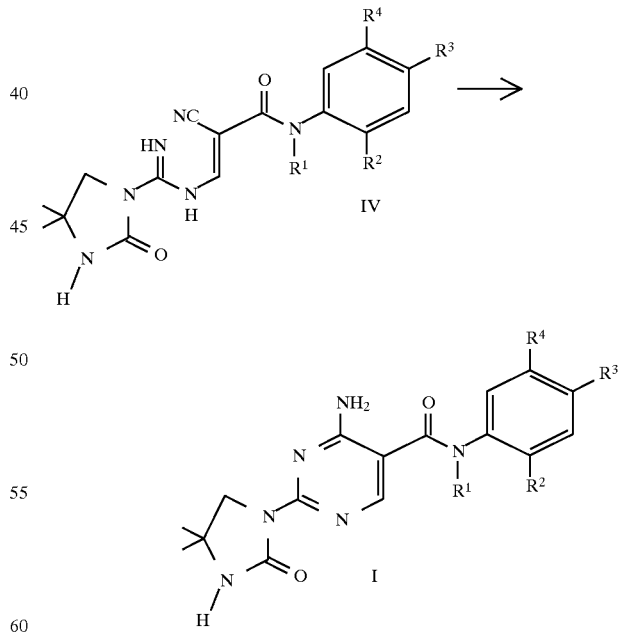

cyclizing a compound of formula IV, wherein R¹, R², R³ and R⁴ are defined as in claim 1, to a form a compound of formula I.

7. A process for preparing the compounds of claim 1, comprising

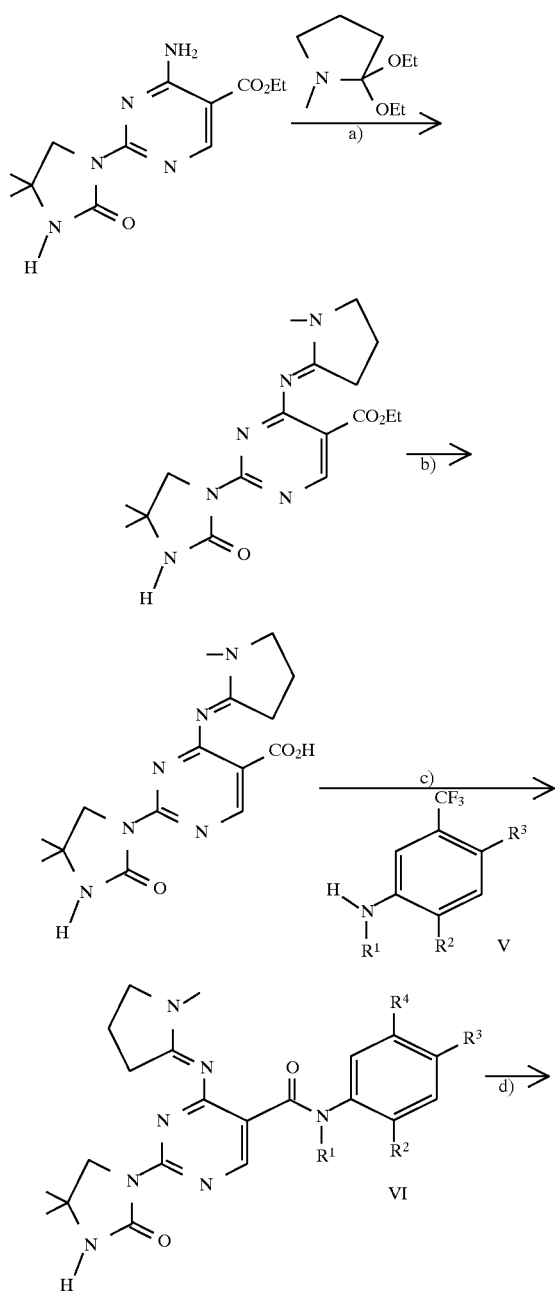

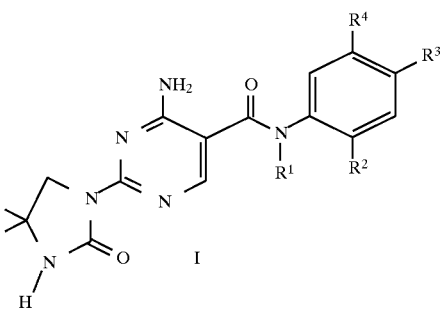

(a) reacting ethyl 4-amino-2-(4,4-dimethylimidazolidin-2-on-1-yl)-pyrimidinecarboxylate with 2,2-diethoxy-1-methylpyrrolidine in a suitable solvent, at a temperature from 0° to 150° C., to give ethyl 4-(1-methylpyrrolidin-2-ylideneamino)-2-(4,4-dimethylimidazolidin-2-on-1-yl)-pyrimidine-5-carboxylate, (b) reacting the ethyl 4-(1-methylpyrrolidin-2-ylideneamino)-2-(4,4-dimethylimidazolidin-2-on-1-yl) pyrimidine-5-carboxylate obtained with NaI and TMSCl in a suitable solvent at a temperature from 0° to 150° C. to give 4-(l-methylpyrrolidin-2-ylideneamino)-2-(4,4-dimethylimidazolidin-2-on-1-yl)-pyrimidine-5-carboxylic acid, (c) reacting resulting the 4-(1-methylpyrrolidin-2-ylideneamino)-2-(4,4-dimethyl-imidazolidin-2-on-1-yl)-pyrimidine-5-carboxylic acid in a suitable solvent at a temperature from 0° to 150° C., in the presence of TOTU and an auxiliary base, with a compound of formula V to form a compound of formula VI, wherein $R^1$, $R^2$, $R^3$ and $R^4$ are defined as in claim 1, and (d) reacting the resulting compound of formula VI, wherein $R^1$, $R^2$, $R^3$ and $R^4$ are defined as in claim 1, in a suitable solvent, at a temperature of 0°–150° C. in the presence of an auxiliary base to give a compound of the formula I.

8. The process of claim 7 wherein the auxiliary base of step (d) comprises aqueous ammonia solution with ethylenediamine.

9. A pharmaceutical preparation, comprising at least one compound according to claim 1 and one or more pharmaceutically suitable excipients.

10. A method for producing a pharmacuetical preparation according to claim 9, comprising admixing said at least one compound according to claim 1 with a pharmaceutically suitable excipient.

11. A pharmaceutical preparation of claim 9, comprising 0.5 to 70 percent by weight of said at least one compound.

12. A pharmaceutical preparation according to claim 9 in a suitable administration form, selected from the group consisting of tablets; coated tablets; capsules; pills; aqueous solutions, suspensions and emulsions; sterile injectable solutions; nonaqueous emulsions, suspensions and solutions; sprays; and preparation forms with protracted release.

13. A pharmaceutical preparation according to claim 9 formulated for oral, parenteral, intraperitoneal or rectal adminstration.

14. A method of treating disorders of lipid metabolism, comprising administering to a patient in need of such treatment an effective amount of at least one compound according to claim 1.

15. A method according to claim 14, wherein the disorder of lipid metabolism is hyperlipidemia.

* * * * *